(12) United States Patent
Hill et al.

(10) Patent No.: US 9,298,877 B2
(45) Date of Patent: Mar. 29, 2016

(54) IMAGE DATA FRAUD DETECTION SYSTEMS

(75) Inventors: Derek Lionel Glendon Hill, London (GB); Kate McLeish, London (GB); Joseph Vilmos Hajnal, London (GB)

(73) Assignee: IXICO Technologies Limited, London (GB)

( * ) Notice: Subject to any disclaimer, the term of this patent is extended or adjusted under 35 U.S.C. 154(b) by 801 days.

(21) Appl. No.: 13/055,847

(22) PCT Filed: Jul. 24, 2009

(86) PCT No.: PCT/GB2009/050920
§ 371 (c)(1),
(2), (4) Date: Apr. 11, 2011

(87) PCT Pub. No.: WO2010/010404
PCT Pub. Date: Jan. 28, 2010

(65) Prior Publication Data
US 2011/0176712 A1    Jul. 21, 2011

(30) Foreign Application Priority Data

Jul. 25, 2008 (GB) .................................. 0813668.1

(51) Int. Cl.
*G06K 9/00* (2006.01)
*G06F 19/00* (2011.01)

(52) U.S. Cl.
CPC .................................. *G06F 19/321* (2013.01)

(58) Field of Classification Search
CPC .............................. G06F 19/321; G06F 19/322
USPC .......... 382/100, 128–132, 305, 307; 705/2, 3, 705/4; 707/687, 690, 769, 770–771; 378/62
See application file for complete search history.

(56) References Cited

U.S. PATENT DOCUMENTS

| 7,860,287 B2 * | 12/2010 | Zahlmann et al. ............ 382/128 |
| 8,370,293 B2 * | 2/2013 | Iwase et al. .................... 707/608 |
| 2002/0051237 A1 | 5/2002 | Ohara |
| 2004/0071333 A1 | 4/2004 | Douglas et al. |
| 2004/0247168 A1 | 12/2004 | Pintsov et al. |
| 2005/0154891 A1 | 7/2005 | Skipper |

(Continued)

FOREIGN PATENT DOCUMENTS

| EP | 1903462 A2 | 3/2008 |
| GB | 2377107 A | 12/2002 |
| JP | 10079732 A | 3/1998 |
| JP | 2002010110 A | 1/2002 |
| JP | 2005018433 A | 1/2005 |
| WO | 9726618 A1 | 7/1997 |

OTHER PUBLICATIONS

Machine translation of Patent Abstracts of Japan Publication No. 10-079732, Mar. 24, 1998, Application No. 08-233362, Sep. 3, 1996, Network Security System and Method Therefor, machine translation MT.*

*Primary Examiner* — Hadi Akhavannik
(74) *Attorney, Agent, or Firm* — Fraser Clemens Martin & Miller LLC; William J. Clemens (57) ABSTRACT

A system is described for detecting fraud from medical imaging data comprising image data and associated metadata. The system comprises input means arranged to receive image data from at least one source, and processing means arranged to analyze the imaging data to determine whether it meets a fraud criterion, and if it does to generate a fraud indicator output.

7 Claims, 4 Drawing Sheets

(56) References Cited

U.S. PATENT DOCUMENTS

| | | |
|---|---|---|
| 2007/0136213 A1 | 6/2007 | Sansone et al. |
| 2007/0143158 A1 | 6/2007 | Cordery et al. |
| 2007/0271183 A1 | 11/2007 | Foth |
| 2007/0292012 A1* | 12/2007 | Brandon et al. ............ 382/128 |
| 2008/0052112 A1* | 2/2008 | Zahlmann et al. ............ 705/2 |
| 2008/0086420 A1* | 4/2008 | Gilder et al. ............ 705/44 |
| 2008/0172741 A1 | 7/2008 | Reumann et al. |
| 2008/0218591 A1 | 9/2008 | Heier et al. |
| 2009/0161925 A1* | 6/2009 | Cottard et al. ............ 382/128 |
| 2013/0124459 A1* | 5/2013 | Iwase et al. ............ 707/608 |

* cited by examiner

| Subject ID | Visit 1 | Visit 2 | Visit 3 | Visit 4 | Visit 5 |
|---|---|---|---|---|---|
| S0010001 | lm1, lm2, lm3 | lm1, lm2, lm3 | lm1, lm2, lm3 | lm1, lm2, lm3 | lm1, lm2, lm3 |
| S0010002 | lm1, lm2, lm3 | lm1, lm2, lm3 | lm1, lm2, lm3 | lm1, lm2, lm3 | lm1, lm2, lm3 |
| S0020001 | lm1, lm2, lm3 | lm1, lm2, lm3 | lm1, lm2, lm3 | lm1, lm2, lm3 | lm1, lm2, lm3 |
| S0020002 | lm1, lm2, lm3 | lm1, lm2, lm3 | lm1, lm2, lm3 | lm1, lm2, lm3 | lm1, lm2, lm3 |
| S0030001 | lm1, lm2, lm3 | lm1, lm2, lm3 | lm1, lm2, lm3 | lm1, lm2, lm3 | lm1, lm2, lm3 |
| S0030002 | lm1, lm2, lm3 | lm1, lm2, lm3 | lm1, lm2, lm3 | lm1, lm2, lm3 | lm1, lm2, lm3 |
| S0030003 | lm1, lm2, lm3 | lm1, lm2, lm3 | lm1, lm2, lm3 | lm1, lm2, lm3 | lm1, lm2, lm3 |
| S0030004 | lm1, lm2, lm3 | lm1, lm2, lm3 | lm1, lm2, lm3 | lm1, lm2, lm3 | lm1, lm2, lm3 |
| S0040001 | lm1, lm2, lm3 | lm1, lm2, lm3 | lm1, lm2, lm3 | lm1, lm2, lm3 | lm1, lm2, lm3 |

*Fig. 5*

IMAGE DATA FRAUD DETECTION SYSTEMS

FIELD OF THE INVENTION

The present invention relates to data management systems and in particular to fraud detection in systems for managing data, such as image data, collected in clinical trials and for medical applications.

BACKGROUND OF THE INVENTION

Fraud is an increasingly recognised problem in clinical trials, and also a matter of concern for healthcare insurance claims and reimbursement. Fraud involves submitting details of fictitious subjects, or data from subjects that exist, but for which all or part of the data submitted was not collected from the correct subject or not collected at the right time or has been deliberately modified in some undeclared way. With the increasing use of images in clinical trials and in healthcare, the impact fraudulent images may have is a significant cause for concern.

SUMMARY OF THE INVENTION

The applicant has appreciated that in order to reduce the impact fraudulent images can have on clinical trial results and in healthcare processes such as clinical audit or for insurance and other reimbursement claims it may be possible to detect fraud through examination of the image data and its associated metadata.

The present invention provides a system for detecting fraud in clinical trials or healthcare applications by examining medical imaging data comprising image data and associated metadata, the system comprising input means arranged to receive image data from at least one source, and processing means arranged to analyse the imaging data to determine whether it meets a fraud criterion, and if it does to generate a fraud indicator output.

According to some embodiments of the invention the processing means may be arranged to identify, when the fraud indicator output has been generated, a subset of the imaging data which met the fraud criterion and isolate for further processing a group of imaging data that excludes the identified subset. The processing means may be arranged to produce respective analysis, such as clinical trial results, from the imaging data and the isolated group of imaging data. Comparison of the results of that analysis will indicate whether or not the excluded subset of the imaging data significantly affects the analysis i.e. if a suspected fraud actually affects the findings on e.g. the efficacy and/or safety of a drug.

In other embodiments of the invention, the processing means may be arranged to identify, when a fraud indicator output has been generated from healthcare data, the individuals or hospitals at which the potential fraud has arisen, and for any suspected data to be quarantined until further investigation has determined whether fraud has indeed occurred.

Preferred embodiments of the present invention will now be described by way of example only with reference to the accompanying drawings.

DESCRIPTION OF THE PREFERRED EMBODIMENTS

Figure 1:
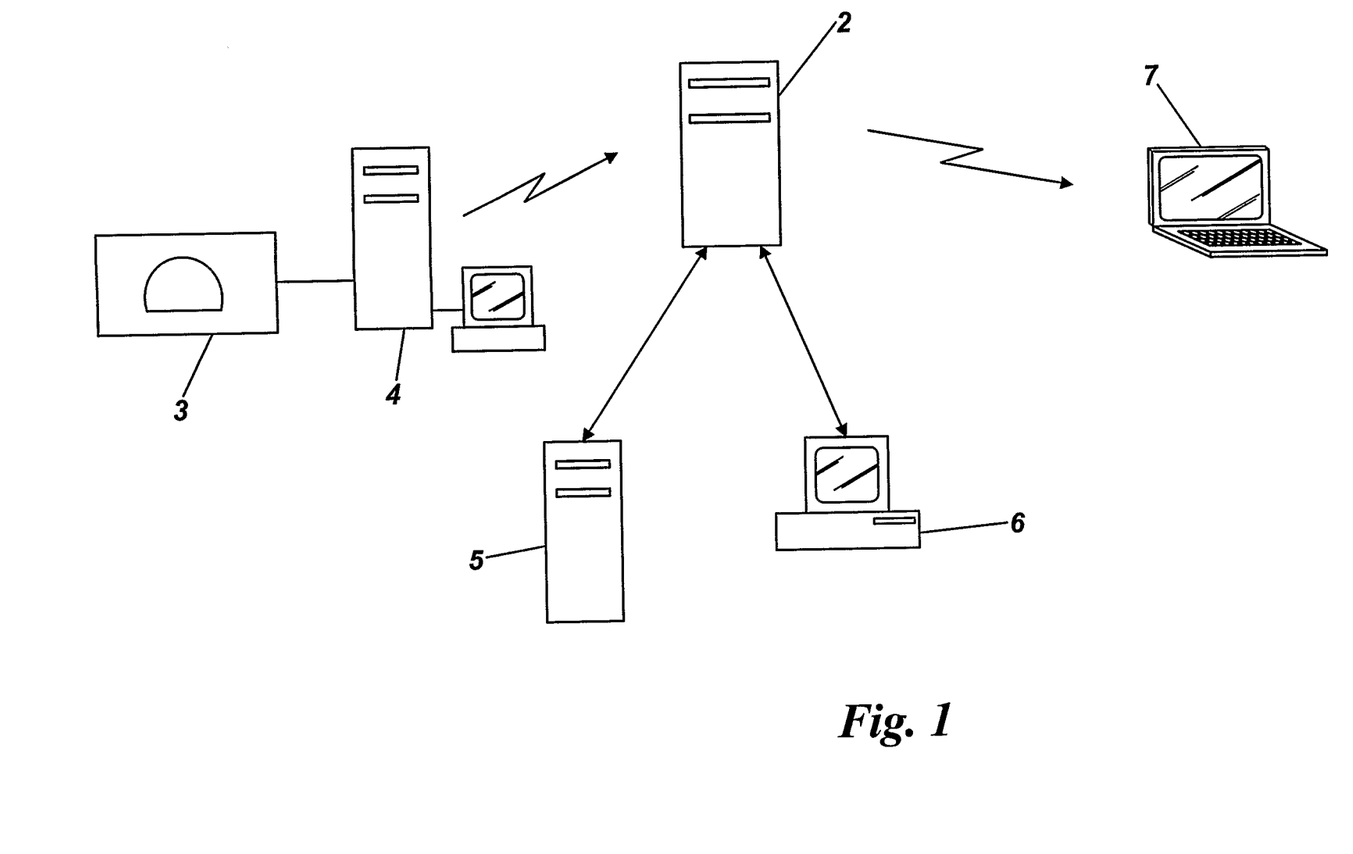
FIG. 1 is a diagrammatic representation of a data management system according to an embodiment of the invention

Referring to FIG. 1, an imaging data management system is arranged to manage data on a central server 2 at a central site. Data can be uploaded from a number of sites, for example from a number of scanners 3 (only one of which is shown) via computers 4 at each scanner site. Tasks can be scheduled to computers 5, if they can be performed automatically, and to workstations 6 if they are to be performed manually. The results of the trial can be reported to a client system 7.

Figure 2:
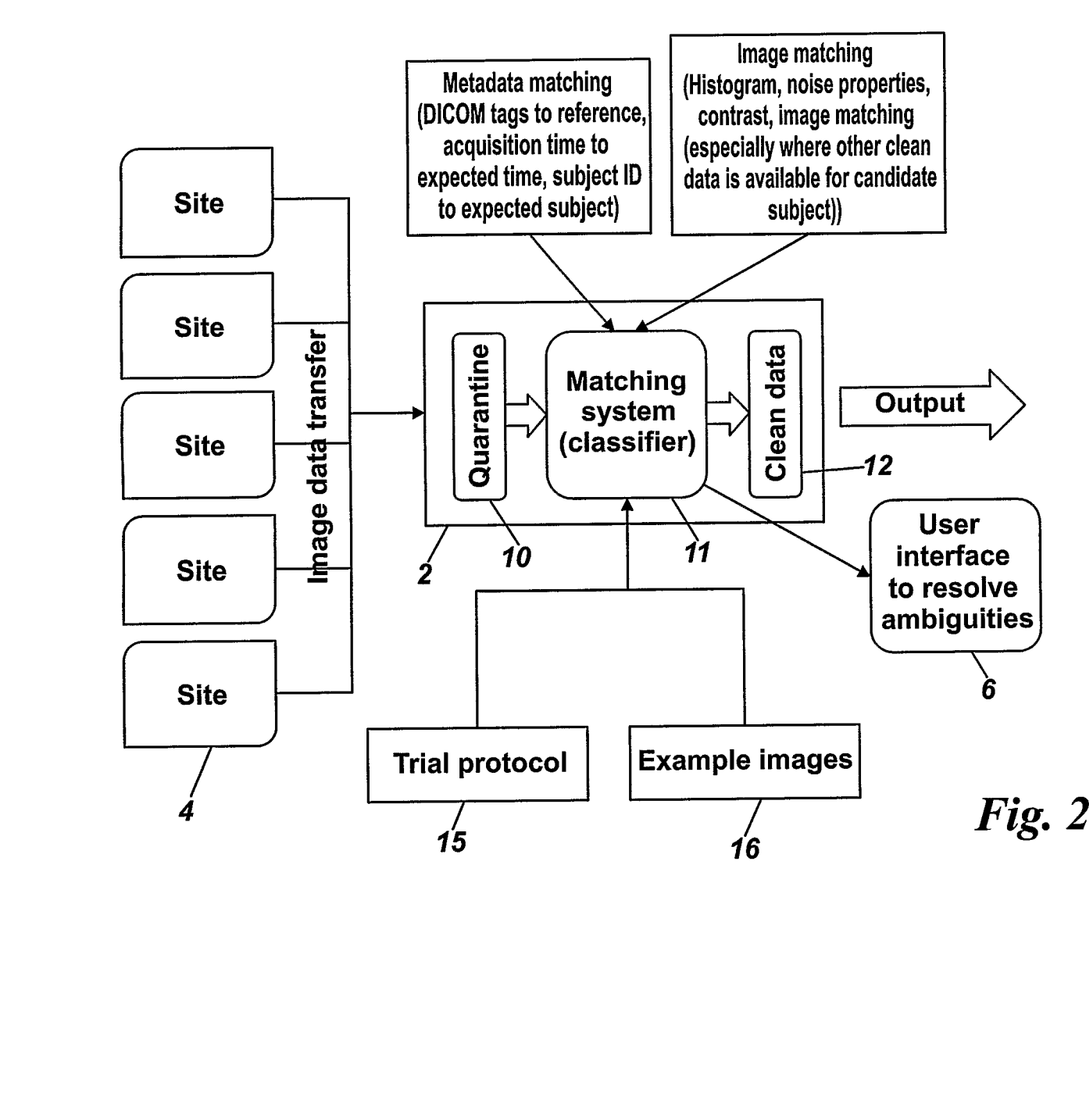
FIG. 2 is a functional representation of a data uploading part of the data management system of FIG. 1.

Referring to FIG. 2, the central server 2 is arranged to receive imaging data, in the form of actual image data, and associated metadata. This may be in the form of DICOM files, and comes from computers 4 at the scanner sites. The central server 2 is further arranged to perform a number of data checking and cleaning tasks, and to output the cleaned data for example to provide reports to the client 7. Performing the data checking and cleaning tasks also improves the accuracy and effectiveness of the later fraud detection operations, as will be described later. The central server 2 includes a first memory area that serves as a quarantine 10 in which incoming data is held, a matching system 11 arranged to perform the various checking and cleaning tasks, and a further memory area 12 for holding the cleaned data ready for exporting (e.g.: for subsequent analysis).

Clinical trials may, because the image data is acquired from multiple sites, have multiple problems including:

The images are typically not labelled consistently between sites, between scanners at a single site, or for images acquired at the same scanner at different timepoints. For example, an MR scan that is T2 weighted might be labelled as "T2w" at one site, "T2 weighted" at a second, and "FSE" at a third. Similar ambiguities will be present in labels in the headers of images from other modalities including CT, PET and ultrasound.

In clinical trials, some sites may correctly enter subject information in a de-identified format (e.g. replace subject name with an identifier, and replace date of birth with year of birth) but this may not be done consistently. Users may also accidentally mis-type the subject identifier. In the clinical context subject details may be incorrect or even completely inappropriate (e.g. examinations for two subjects interchanged).

Numerous different combinations of hardware and software are used in scanners, so the images will be acquired slightly differently at different sites involved in a multi-centre clinical trial, or at different hospitals providing care for patients undergoing diagnosis and treatment according to a similar protocol. For the data to be considered standardized, variations between sites should be within a defined range, and each site should apply the same acquisition protocol consistently for all subjects they scan at all time points.

Some data is missing, because of transfer errors, because of failure of the site to follow the protocol, because the subject did not attend an appointment, or because the subject could not remain in the scanner for the full examination.

There may be unexpected data (eg: scans repeated due to motion, scans obtained because an unexpected change in the disease or a possible side effect (adverse event) was being investigated)

Data may be sent that is from the wrong trial or from the wrong clinical examination Associated data (metadata) that is not in the image header, but is important for the analysis of the image data may similarly be missing, mis-labelled or incomplete.

The central server 2 is therefore arranged to use prior information about the images and associated data (metadata) that is expected which typically includes any one or more of the following:

1. Details of the modality of the scan, i.e. the type of scanner, and as each type of scanner can collect various types of image, details of the type of scan (including expected values of selected DICOM metadata value)
2. The number of visits by each subject, and the timing of the visits, for example defined in terms of time intervals between visits (in some circumstances, the total number of visits may not be defined, but the interval between them is, and the subject will repeatedly be re-imaged until a defined event happens eg: their disease starts getting worse)
3. The format of the subject identifiers and expected format of the date of birth of the subject
4. Example images of the different types
5. Examples of the non-image data of the required types (eg: physiological data)
6. Information about the required labels (subject related and scan related), and the expected label value or values.

Some or all of this reference data is stored in a trial or clinical examination configuration file, which is derived from the trial protocol or healthcare protocol or histology protocol 15. For a clinical trial, the protocol is generated when the trial is planned and, the derived trial configuration file is stored on the central server 2. In some cases some of the data, such as example images, may be stored in a separate image file 16. In healthcare applications, a protocol is defined for the treatment of patients that have similar symptoms, diagnoses or are undergoing similar treatments, and these protocols are also known in advance—though may be more flexible than clinical trial protocols.

The central server 2 matches in-coming imaging data comprising the image data and metadata (either arriving in bulk after the trial is completed, or arriving gradually during the course of the trial) against the prior knowledge about what is expected in order to allocate correct labels to the required image attributes. The matching involves analysis of the metadata, and of the image data itself (with respect to reference data and previously collected data). Data is quarantined while this matching is going on, and any data for which the match confidence is below a defined threshold is left in quarantine for inspection by a user. While the description below refers to images in DICOM format, any other suitable format or formats can be used, and metadata includes (but is not limited to) data in the image headers, in associated files, in the file names and in the directory structure of the computer system.

The matching, or some aspects of it, is performed in a combined multidimensional classifier space. The dimensions correspond to different properties of the imaging data, such as values of parameters defined in the metadata or properties of the image data. For example the matching includes: matching metadata values in the incoming data against the reference metadata values. These metadata values can therefore define one or more dimensions of the classifier space. Other dimensions can relate to image derived measures such as intensity histograms. The image intensity histograms can be quite distinct for a particular type of image acquisition, and can be calculated by plotting voxel intensity (brightness) on the horizontal axis, and frequency of occurrence of this brightness on the vertical axis. Incoming data can therefore be matched to expected data by determining the proximity between the two in the multi-dimensional classification space. Once the closest match has been found a confidence parameter dependent on the proximity is associated with the match, and the incoming data can be corrected if appropriate.

As more data is passed through the system, the classifiers can learn more about the expected study or clinical data to increase the confidence of the labelling.

Figure 3:
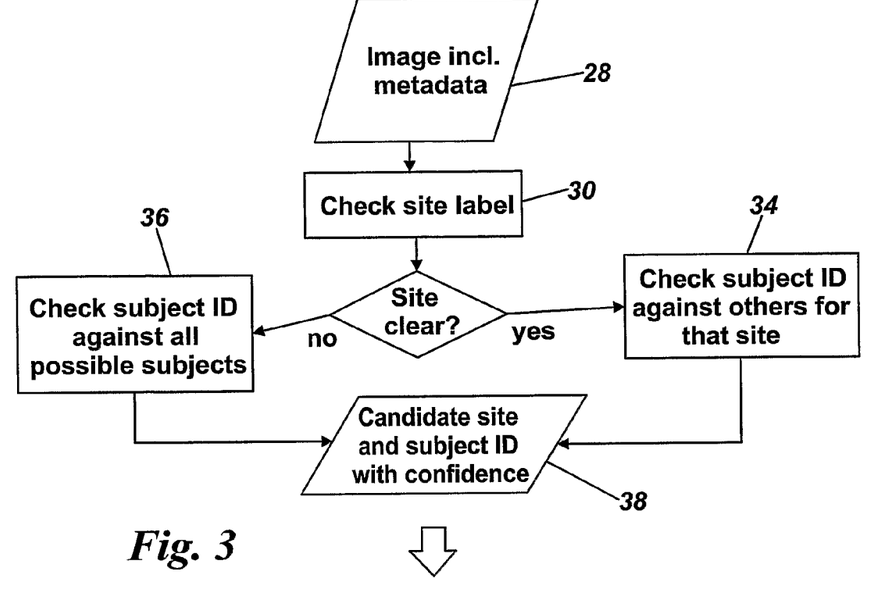
FIG. 3 is a flow diagram showing part of the operation of the system of FIG. 1.

Referring to FIG. 3 one part of the checking of incoming image data files includes checking at step 30 the site label which indicates the site at which the scan was performed. If the site label is unambiguous (eg: it is in the correct format and corresponds to a site for which data collected at that timepoint is expected), then the process moves to step 34 where it checks the subject ID against other IDs associated with that site. If the site label is ambiguous, then the process moves to step 36 where it checks the subject ID against all possible subject IDs from all sites to identify the closest match. From the closest, or identical, subject ID the correct site with which that subject is associated can be identified. From either of steps 34 or 36 the server can generate at step 38 a candidate site and subject ID with a confidence level indicating a probability that the candidate data is correct.

Figure 4:
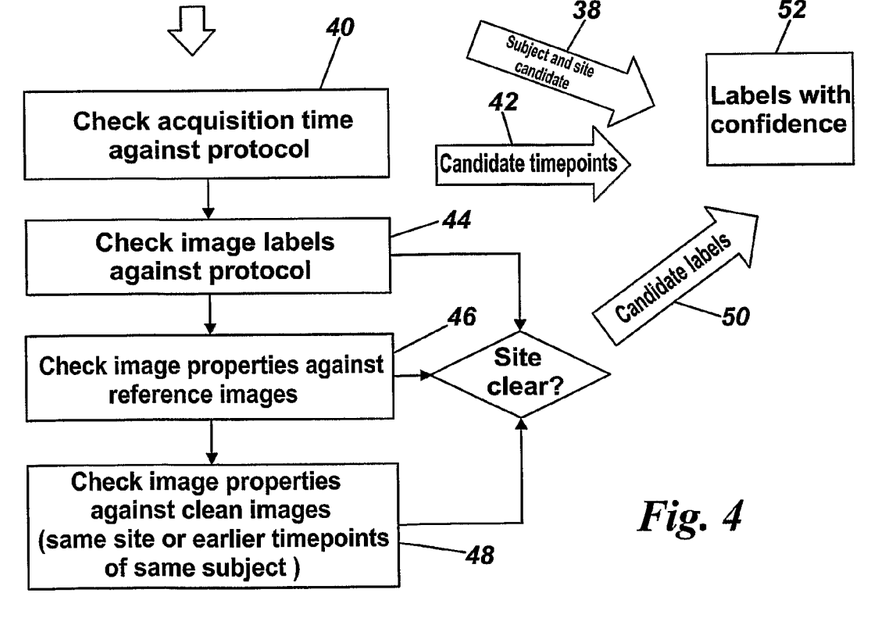
FIG. 4 is a flow diagram showing part of the operation of the system of FIG. 1.

Referring to FIG. 4, in a further part of the checking process, the acquisition times indicated in the DICOM file metadata, for the associated images in the received data, are checked at step 40 against the expected acquisition times defined in the trial configuration file. This comparison identifies the most likely acquisition time point for each image, which is used as a candidate time point 42, and those candidate time points with associated confidence levels are also output. Then at step 44 the server 2 checks the image labels in the received DICOM file against the labels in the trial configuration file, and identifies the most likely image labels together with a confidence level. As with the subject ID, the check can be against expected labels for the site identified in the DICOM file, if that is matched to a valid site, and against expected labels from all sites if there is no valid site match. Then at step 46 various properties of the images in the DICOM file are determined, by analysis of the image data, and compared with corresponding properties of the appropriate reference images 16. Properties which may be used for this comparison include the noise spectrum of the image, i.e. the level of noise as a function of spatial frequency, the signal to noise ratio of the image, image intensity ratio, image histogram metrics including information theoretic measures (e.g. mutual information) skewness or similarity of match with a reference image histogram or image features, i.e. parts of the image data corresponding to imaged parts of the subject. At step 48 the various image properties of the received images are compared with the corresponding properties of clean images from the same site, or earlier images from scans of the same subject at earlier time points.

At each of steps 46 and 48, each of the properties which is compared has one or more labels or parameters associated with it. For example the noise spectrum of the image may be unique to a particular scanner, or a particular scanner type, and therefore a reference noise spectrum may be indicative of the image having been acquired on a particular scanner or type of scanner. Therefore the degree of similarity between the noise spectrum of the received image and those of a number of reference images may identify the scanner on which the received image was acquired, with an associated confidence determined by the degree of similarity. Reference image features may be associated with particular scan parameters, for example the part of anatomy being scanned, or the orientation of the subject during the scan. These parameters will generally be defined in the trial protocol file by means of associated metadata or labels. Therefore checking the image features against reference images can be used to identify candidate scan parameters of this nature. A further aspect of the checking relates to the metadata that labels the type of image collected (e.g. in DICOM this is called the series description). That data is compared with other metadata to confirm that it is consistent with that, and also with properties of the image data, which depend on the type of scanner used or the type of scan performed, to check that it is consistent with that data.

Once the checks described above have been completed, a complete candidate set of metadata, (or labels) with associated confidence levels can be defined.

Figure 5:
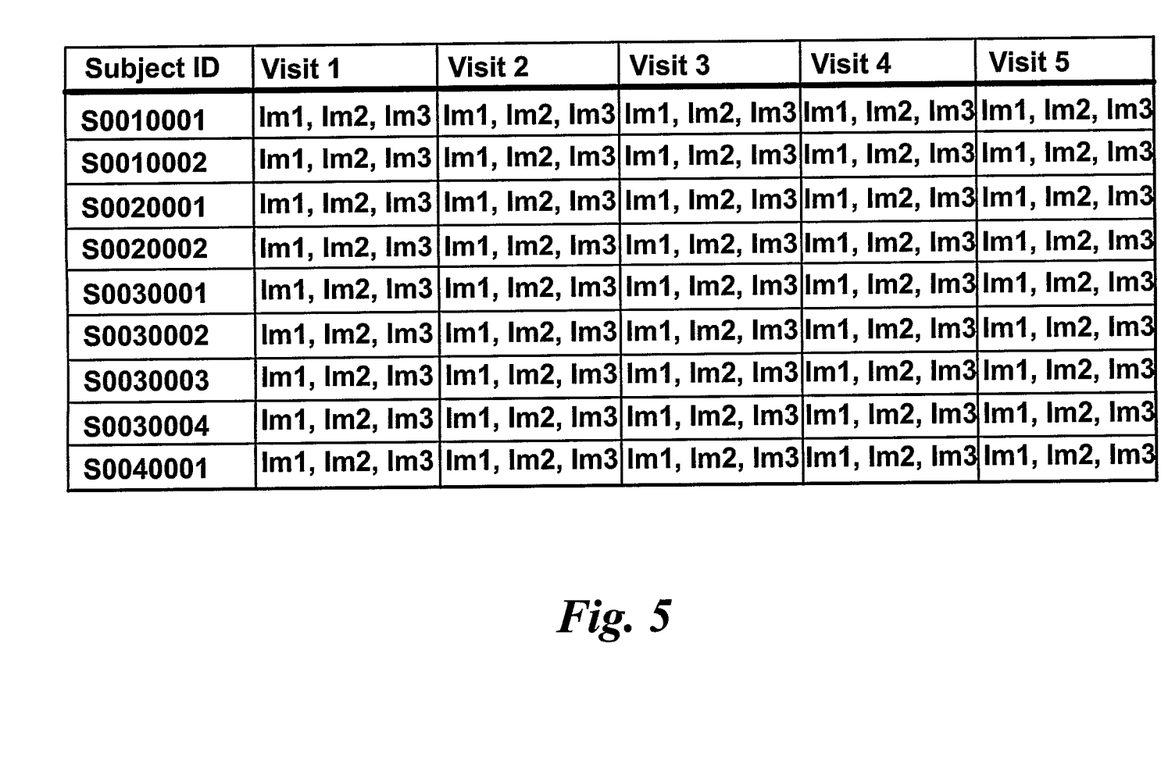
FIG. 5 is a table showing part of an image data set used in the system of FIG. 1.

Referring to FIG. 5, an example of a trial protocol defines a number of subject identities, a number of visits that each subject is expected to make to the scanner site including site identification and acceptable ranges of times for the visits, and a number of different scan images that need to be acquired at each visit, including the type of scanner and the type of image to be acquired with the scanner. The acceptable range of times may be defined in absolute terms, but are more likely to be in terms of time intervals between each visit and the previous one, or each visit and a reference time point, such as a start date of the trial or treatment regime. These definitions of the different expected images therefore include data defining labels, characteristics and features of the expected images. In the example shown three images are required of each subject at each visit. The timing of the visits is also defined, typically in terms of an acceptable range of time intervals between each consecutive pair of visits. Referring back to FIG. 2, once the data cleaning has been performed on an individual image file, the matching system is arranged to identify a candidate image definition, i.e. a candidate location in the table of FIG. 5, for that image file. Again this can be associated with a degree of confidence. As the data is received, it can be displayed in a table such as that of FIG. 5 with each of the expected images highlighted in a colour to indicate its current status. In this case one colour, such as green, is used to indicated clear data, another such as amber, is used to indicate ambiguous data, which needs further checking, and another colour such as red is used to indicate data that is missing.

At each stage of the checking described above, the confidence level is checked. If it is above a predetermined limit, which can be set independently for each parameter, then the image data, or the metadata, of the received imaging data file can be corrected or left as appropriate so that it corresponds to the reference data. For example, if the subject ID is very close to, but slightly different from, a valid ID, then it can be corrected automatically. If all the data in the imaging file suggest that it came from one particular scanner, apart from the scanner ID in the file metadata, then assuming the confidence is high enough the scanner ID can be corrected automatically. In other cases, where an exact match, or a match with sufficiently high confidence, cannot be found, then this can be flagged to a user for review. For example this can be done by displaying the image, and any associated metadata that is not in doubt on the display of the user interface 6, together with a list of the most likely options for the data or label that is in doubt. A user can then make the appropriate selection to correct the data by providing a suitable input at the user interface 6.

The embodiment described provides a much more automated solution to data checking and cleaning compared to previous solutions, reducing the likelihood of mislabelled data being analysed, and providing at-a-glance information about protocol compliance from all study sites. In some case it may be possible to avoid the option of human interaction altogether, but where some cases are referred to a user for review, checking and correction as described above, the rate at which the user will have to intervene will be considerably less than in previous more manual methods.

In some cases the system can be used prospectively, in that the matching system on the server 2 is arranged to monitor the expected time of arrival of image data as defined in the trial protocol, and detect non-arrival of expected data at an expected arrival time. This can be referred to an operator to check or flagged in the report data as an error.

In all cases where the imaging data is amended, a full audit trail of all data cleaning activity and other data amendments is recorded, for example in the file containing the imaging data. This allows the audit trail to be kept and checked as required.

It will be appreciated that, though the embodiment described includes a central server that performs the data checking and cleaning, it is equally possible for the system to be a distributed system in which various different functions or tasks are performed on different computers, which may be remote from each other.

Fraud Detection

The server 2 is also arranged to monitor the incoming data for signs of fraud, which might involve, for example, any one or more of the following:

1. Investigators submitting the same image multiple times (to simulate multiple subjects from one subject, or to simulate multiple scans of the same subject from one scan at one time point).
2. As 1. above, but with different metadata (scan data, subject ID, subject d.o.b. etc.) attached to the different copies of the image data.
3. As 1. or 2. above but with some simple image modification applied to one or more of the copied images, for example adding noise to the image, or a smooth transformation of the image.
4. Investigators participating in multiple trials could submit the same subject, and the same image data from that subject, to different sponsors.
5. Investigators could submit images from non-trial subjects (e.g. normal hospital patients)
6. Investigators could generate data to submit for one subject from a variety of other patients or subjects (e.g. one modality from one patient and another modality from a different patient, or within one modality that has multiple scans, one scan from one subject, one from another)

It will be appreciated that the consistency checks described above with reference to FIGS. 1 to 5 can be used, rather than for correction and cleaning of the data, as a check for fraud. Where inconsistencies are detected, rather than being corrected as described above they can be flagged to a user as an indication of potential fraud. Therefore in one embodiment of the invention, the central server 2 (though it could equally be a different computer system) is arranged to compare all the images collected from a particular site, or indeed all sites, to look for evidence of fraud. This comparison may be made for data collected from a single trial, or for data collected from multiple trials (for example by a regulator looking for evidence of sites committing fraud for multiple trial sponsors). The computer system performs a mixture of image metadata analysis and image analysis to detect possible fraud. The metadata associated with the images may be included in the image files (e.g. DICOM tags), in other associated files or in the file and directory names. The metadata will typically contain information about the subject (identifier, date of birth, weight etc.) and also about the scan (the scan parameters used to collect the images). This metadata can be analysed, for example by comparing the DICOM files between different trial subjects from a given site, to detect the possibility that this metadata has been "doctored" to make the different image files appear to relate to scans on different subjects when in fact they relate to the same subject, or indeed to appear to relate to the same subject when in fact they relate to different subjects.

In many cases the correction and cleaning of the data that has already been performed will eliminate or at least mitigate mis-detections of fraud resulting from errors in the data. Where a sufficiently high confidence level was assigned, errors will have been corrected, so these errors will not be mis-detected as fraud.

Stored on the server 2 are fraud criteria that are used to assess whether or not imaging data is fraudulent. The server 2 is arranged to analyse the imaging data to determine whether it meets one or more stored fraud criterion. Respective fraud criteria relate to different ways in which imaging data may be fraudulently manipulated or altered, and include threshold values and/or rules. If a threshold value is exceeded by the imaging data being analysed, or a rule is met, the imaging data being analysed has likely been manipulated or altered fraudulently. When imaging data has been found to meet one or more fraud criterion, the server 2 generates a fraud indicator output.

The fraud criteria will now be described in more detail, with reference to the different fraudulent acts to which they relate.

The most primitive type of fraud is to submit the same image data multiple times, without even modifying the subject identifier information. In this case, the digital image data, and some or all of the metadata, would be identical across respective files. The server 2 is therefore arranged to perform a simple file comparison between all files submitted, or specific sets of the files submitted, to detect this. In this case the fraud criterion stored on the server 2 includes a rule to indicate that if any two files, or two files from a set, are identical the server 2 generates a fraud indicator output. This output may be external and, for example, affect how the server generates feedback to a user, or internal and affect, for example, how the server continues to process the data.

A slightly more sophisticated fraud would involve submitting the same image data multiple times, but editing the metadata to change the subject identifier and scan dates. This would mean that the image data in the respective image files is no longer identical, but the pixel intensity values are. The server 2 is arranged to detect this type of fraud using a simple comparison of the image data (e.g. image subtraction of the intensity values of the individual pixels of the images, which will generate zeros on comparison of two identical images) can detect this fraud. The comparison can also be performed by considering the ratio of the intensities of the pixels in the respective images, where ratios of approximately 1:1 indicate that all the pixels are the same, which can be indicative of fraud. In this case the fraud criterion stored on the server 2 includes a rule to indicate that if any two files have identical (or very similar) intensity values a fraud indicator output is to be generated.

With widespread availability of image editing software (e.g. Adobe photoshop), a more sophisticated fraud would involve making changes to the image intensity data. For example, the images from one subject could be simulated by adding noise to or warping an image from a different subject.

Similarly images of a subject from multiple timepoints could be simulated from a single image taken at a first time point by the same types of image modification. The server 2 is therefore arranged to detect these changes by looking for images that differ from each other by noise of some known characteristic or by a smooth transformation. The noise characteristics are measured relative to reference data from other images in the same trial. The associated fraud criterion stored on the server 2 includes a number of noise characteristics and transforms, and if the server finds noise characteristics or a transform identical (or very similar) to those stored it generates a fraud indicator output. As noise can be specific to a particular scanner or type of scanner, a comparison of noise in images submitted from the same scanner, or type of scanner, is used to verify the scanner identity given for each file.

The server 2 is also arranged to detect fraud that is based on submitting images of non-trial subjects e.g. subjects from a different trial, or subjects who were not recruited for the trial for which the data is submitted. The server 2 detects this type of fraud by detecting images that do not have the same metadata properties as the other images submitted for the trial, or as expected from that site's qualification process. This would suggest that the site is not following the protocol provided, but using images acquired according to another protocol. In this case the fraud criterion stored on the server 2 includes a rule to indicate that if any two files from the same trial have more mutually different parameters in their metadata than a predetermined threshold a fraud indicator output is to be generated. The server 2 can also look for images that have different intensity properties to other images acquired in that same trial (detected using methods including analysis of the image histogram and of the image contrast properties). This latter approach would detect fraudulent images that were acquired with the wrong protocol (e.g. a protocol for a different trial) but where the metadata had been modified to make it look as if the correct trial protocol had been followed.

The server 2 is also arranged to detect fraud by detecting whether the images submitted are consistent with the expected age of subjects for the trial (which can be detected from the images even if the patient date of birth tag has been fraudulently entered by the investigator). For brains, this works by comparing subject images with images from a normal aging cohort to identify whether the geometrical properties of the brain are consistent with the stated age of the subject. In this case the associated fraud criterion stored on the server 2 includes brain geometrical properties for a number of cohorts. If the properties of the compared image are not identical (or very similar) to those of the images in the corresponding stored cohort a fraud indicator output is to be generated.

If an investigator at a site submits image data that is stated to come from one subject, but in reality comes from multiple subjects (e.g. to enable that investigator to submit the right types of image data to adhere to the trial protocol), then the system will detect this by identifying differences in image geometrical properties that suggest the images are from subjects that have different anatomy. In this case the fraud criterion stored on the server 2 includes a rule to indicate that if any two files relating to the same subject have more mutually different geometrical properties than a predetermined threshold a fraud indicator output is to be generated.

The above methods are all based on the assumption that no changes can be made to the acquired data for the sake of monitoring for fraud. In some embodiments, more control is given to the image acquisition, and it is possible to build into the image file metadata or the actual image data a digital watermark to protect against fraud. The simplest form of watermark would be a unique identifier, e.g. generated from scanner ID and date and time when the image was scanned, in the DICOM header or coded into the images (written into a blank line at the start, or distributed throughout an image). Such a watermark can be applied in the scanner (which requires that it be implemented by the scanner vendor), or added as part of a process of exporting the data from the scanner. The acquisition date indicated in the watermark can then be checked against the date the file was transferred, and if these dates are inconsistent, or indicate that the image was acquired too early to meet the requirements of the trial protocol, then the server 2 generates a fraud indicator output.

The fraud detection aspects of some embodiments make use of the fact that image data (both the pixel/voxel values and the metadata) contain information that can be used to detect fraud. The use of image intensity modelling methods can be used to detect outlier images that may indicate the protocol has not been followed, even if the metadata suggests that it has.

The system can either be run prospectively as data is collected to detect possible fraud, or can be run retrospectively on data that has been collected in completed trials, and can be run on image data from a single trial or from multiple trials.

The fraud detection analysis will be performed on the checked and cleaned data stored in the further memory area 12. When the server 2 runs the fraud detection retrospectively on the data from a complete trial or trials, this stored data will relate to numerous images from different subjects and, in some cases, from different trials and different sites. In this case, the server 2 is arranged to analyse all of the data to detect fraud, and to identify data that has met a fraud criterion. Thus when a fraud indicator output is generated, the fraudulent data that caused its generation is identified and this identity is stored in a fraudulent data log. Optionally, the fraudulent data log may also be updated to store information related to the fraudulent data, such as the subject, location and/or trial to which it relates, along with any other pertinent related information.

It is very important to understand the impact of a potential fraud on the outcome of clinical trials, e.g. the assessment of a drug's efficacy and/or safety. To that end, the server 2 is arranged to identify a subset of the imaging data which contains the imaging data that met a fraud criterion, and to identify a group of imaging data that is to proceed for further processing. The server 2 then determines the effect that the subset has on the outcome of the clinical trials. This is achieved by identifying two sets of imaging data on which statistical analysis is to be performed, e.g. to determine a drug's safety and/or efficacy. The first set comprises all of the imaging data, including the identified subset of potentially fraudulent data. The second set comprises the group of imaging data identified for further processing, but excludes the identified subset of potentially fraudulent data. Therefore, statistical analysis of the second set of data can be considered to be a re-analysis of the imaging data with potentially fraudulent data having been excluded. The server 2 then proceeds to compare the outcome of the analysis on the first set of data with that of the second set of data. The result of the comparison may be stored and/or output in a report which includes any salient features of the differences between the outcomes. For example, these features include the differences in metrics (e.g. safety and efficacy metrics) between the two, expressed in terms of percentages, and whether the differences were such that one set of data led to predefined thresholds being met and the other set of data led to the same thresholds not being met.

The server 2 is arranged to generate a further investigation indicator output when the potential fraud is determined to be highly significant to the trial results (e.g. when exclusion of the subset changes whether or not a drug meets safety or efficacy thresholds, or leads to a difference in percentage terms above a predefined level). The further investigation indicator output includes some or all of the generated report on the result of comparing the two sets of data, and identifies the imaging data that has caused this effect, including an identification of the subjects, trials, sites, investigators and dates involved. The further investigation indicator output also acts as a trigger causing the server 2 to take further, predefined steps to verify the fraud and/or mitigate the effect of the fraud.

For reasons of clarity, preferred embodiments of the invention have been described above with reference to various steps and tasks being performed by the server 2. It will be clear to those skilled in the art, however, that the steps/tasks may be implemented by alternative suitably configured computer device(s) such as a single desktop computer or server, or a network of suitably-configured computer devices such as desktop computers, servers, portable computers, personal digital assistants (PDAs), servers and the like. The server 2 or the device(s) can be suitably configured by computer interpretable instructions received via a computer readable medium such as a disk (e.g. a floppy disk, CD or DVD), a solid-state storage device, a downloaded electronic signal or any other medium suitable for transferring instructions to a computer device.

Respective steps may therefore be performed sequentially using one or more processors, or concurrently using a plurality of processors. For example, analysing image data to determine whether it meets a fraud criterion may be performed on a first processor, whereas producing trial results may be performed on a second, separate processor on a separate device. Furthermore, the described embodiments advantageously carry out data correction and cleaning before fraud detection to improve the efficiency and accuracy of the fraud detection. Alternatively, they may be performed concurrently and independently, e.g. on separate systems, within the scope of the invention. It is not essential that the data correction/cleaning is performed before the fraud detection.

While the embodiment described above relates to the use of the system in clinical trials, the same invention also be applied to healthcare data that is being aggregated for purposes such as clinical audit or evidence-based-medicine. In such cases, the fraud indicator generated can be used to exclude any potentially fraudulent data from any subsequent analysis that might otherwise be used to draw incorrect conclusions about patterns of care and benefits arising from the imaging studies.

The invention claimed is:

1. A system for detecting fraud from medical imaging data including image data and associated metadata, the system comprising:
   input means arranged to receive the medical imaging data from at least one source; and
   processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;
   wherein the processing means is arranged to compare at least one parameter of the image data with a corresponding reference parameter, and the fraud criterion relates to the similarity of the parameters;

the processing means is arranged to compare one image with another using image subtraction; and the fraud criterion relates to residuals of the image subtraction.

2. A system for detecting fraud from medical imaging data including image data and associated metadata, the system comprising:

input means arranged to receive the medical imaging data from at least one source; and processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;

wherein the processing means is arranged to perform analysis of noise properties of an image being analyzed, and the fraud criterion is arranged to be indicative of image warping.

3. A system for detecting fraud from medical imaging data including image data and associated metadata, the system comprising:

input means arranged to receive the medical imaging data from at least one source; and processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;

wherein the processing means is arranged to compare at least one parameter of the image data with a corresponding reference parameter, and the fraud criterion relates to the similarity of the parameters, the processing means is arranged to compare one image with another using image registration, and the image registration method is based on the use of b-splines to generate a model from cohorts.

4. A system for detecting fraud from medical imaging data including image data and associated metadata, the system comprising:

input means arranged to receive the medical imaging data from at least one source; and processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;

wherein the processing means is arranged to compare at least one parameter of the image data with a corresponding reference parameter, and the fraud criterion relates to the similarity of the parameters, the reference parameter is derived from reference image data, and the processing means is arranged to compare all images indicated as being from single subject and to identify any inconsistencies indicating that they do not appear to be from the same subject.

5. A system for detecting fraud from medical imaging data including image data and associated metadata, the system comprising:

input means arranged to receive the medical imaging data from at least one source; and processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;

wherein the processing means is arranged to compare at least one parameter of the image data with a corresponding reference parameter, and the fraud criterion relates to the similarity of the parameters, the reference parameter is derived from reference image data and the reference image data is from the same subject as an image being analyzed, and the processing means is arranged to identify changes between images from the subject and to compare the changes with changes in the images from a plurality of reference subjects.

6. A system for detecting fraud from medical imaging data including image data and associated metadata, the system comprising:

input means arranged to receive the medical imaging data from at least one source; and processing means arranged to analyze the medical imaging data received by the input means to determine whether it meets a fraud criterion, and if the medical imaging data does meet the fraud criterion to generate a fraud indicator output, the image data including values for each of a plurality of pixels or voxels that make up the image represented by the image data;

wherein the processing means is arranged to identify, in response to a fraud indicator output, a subset of the imaging data which met the fraud criterion and identify for further processing a group of imaging data that excludes the identified subset, and the processing means is arranged to produce respective clinical trial results from the imaging data and the identified subset of imaging data.

7. A system according to claim 6 wherein the processing means is arranged to compare the respective trial results to determine the significance of the excluded identified subset.

* * * * *